United States Patent
Sabate Elias et al.

(10) Patent No.: US 8,802,691 B2
(45) Date of Patent: Aug. 12, 2014

(54) DOMPERIDONE AT A LOW DAILY DOSE FOR USE IN THE TREATMENT OR PREVENTION OF A DISEASE ASSOCIATED WITH AN ALTERATION OF THE IMMUNE RESPONSE

(75) Inventors: David Sabate Elias, Barcelona (ES); Josep M. Homedes Beguer, Barcelona (ES); Pablo Gomez Ochoa, Zaragoza (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 170 days.

(21) Appl. No.: 13/260,156

(22) PCT Filed: Mar. 30, 2010

(86) PCT No.: PCT/EP2010/054177
§ 371 (c)(1),
(2), (4) Date: Nov. 15, 2011

(87) PCT Pub. No.: WO2010/112497
PCT Pub. Date: Oct. 7, 2010

(65) Prior Publication Data
US 2012/0065167 A1 Mar. 15, 2012

(30) Foreign Application Priority Data
Mar. 31, 2009 (EP) .................................. 09382040

(51) Int. Cl.
*A61K 31/44* (2006.01)
*A01N 43/40* (2006.01)
*A61K 31/4164* (2006.01)
*A01N 43/50* (2006.01)

(52) U.S. Cl.
USPC ............ 514/282; 514/322; 514/387; 514/396

(58) Field of Classification Search
USPC .................................. 514/282, 322, 387, 396
See application file for complete search history.

(56) References Cited

U.S. PATENT DOCUMENTS

| 5,372,818 A | 12/1994 | Cross et al. |
| 6,224,895 B1 | 5/2001 | Cross |
| 2001/0005724 A1 | 6/2001 | Cross |
| 2003/0216355 A1 | 11/2003 | Engel |
| 2004/0242543 A1 | 12/2004 | Engel |

FOREIGN PATENT DOCUMENTS

| EP | 0 848 954 A1 | 6/1998 |
| ES | 2 246 142 A1 | 2/2006 |

OTHER PUBLICATIONS

International Search Report issued Jul. 26, 2010, in PCT/EP2010/054177.
Pablo Gomez Ochoa, et al., "Domperidone Against Leishmaniasis: Preliminary Results from First Therapeutic Trial", Oral Communications: Infectious Diseases: Domperidone, Oct. 27, 2002, 1 page (corr. to ES 2 246 142 A1).
Anthony Bryceson, "A policy for leishmaniasis with respect to the prevention and control of drug resistance", Tropical Medicine and International Health, vol. 6, No. 11, XP-002536222, Nov. 2001, pp. 928-934.
Pablo Gomez Ochoa, et al., "Use of domperidone in the treatment of canine visceral leishmaniasis: A clinical trial", The Veterinary Journal, vol. 179, No. 2, XP-025872319, Feb. 1, 2009, pp. 259-263.

*Primary Examiner* — Renee Claytor
(74) *Attorney, Agent, or Firm* — Oblon, Spivak, McClelland, Maier & Neustadt, L.L.P.

(57) ABSTRACT

The invention relates to the use of domperidone or a pharmaceutically acceptable salt thereof at low doses to prevent and/or treat a disease associated with an alteration of the immune response such as Leishmaniosis.

16 Claims, No Drawings

DOMPERIDONE AT A LOW DAILY DOSE FOR USE IN THE TREATMENT OR PREVENTION OF A DISEASE ASSOCIATED WITH AN ALTERATION OF THE IMMUNE RESPONSE

BACKGROUND OF INVENTION

1. Field of the Invention

The invention relates to the use of domperidone or a pharmaceutically acceptable salt thereof at low doses to prevent and/or treat a disease associated with an alteration of the immune response such as Leishmaniosis.

2. Description of the Related Art

Canine Leishmaniosis is a parasitical disease which is endemic in the countries of the Mediterranean basin where seroprevalence may reach a value of 48.4% (Alvar et al. 2004, Paradies et al 2006).

*Leishmania* parasites, similarly to what has also been described for other intracellular pathogenic agents, are able to survive and reproduce in the organism of infected dogs thanks to their capacity to deviate the cellular type immune response (Th1) to the humoral type immune response (Th2). Actually, clinical evolution of the disease depends mainly of the immune response developed by the animal once it has been infected. Thus an infected animal will resist the progression of the disease while it manages to maintain a predominance of the cellular immune response (Th1), with a marked production of type Th1 cytokines, such as Interferon gamma o Interleukine IL-2, which are responsible for the macrophage's activation and, through it, for their leishmanicidal potential. Conversely, when humoral response (Th2) becomes predominant, which may occur immediately after infection or after a more or less prolonged period of resistance to disease progression, the animal succumbs to the disease and starts presenting clinical signs that may even lead to death (Chamizo et al. 2005, Brachelente et al. 2005).

In dogs, resistance to the disease appears to be associated to certain balance between Th1 and Th2 responses although cellular response (Th1) seems to predominate. In species such as the mouse, disease progression or animal resistance to the disease depends on a complete polarization of the immune response towards humoral (Th2) or cellular (Th1), respectively. (Chamizo et al. 2005, Brachelente et al. 2005)

Therefore, the progression of the illness seems to be due to an alteration of the equilibrium between the cellular type immune response (Th1) and the humoral type immune response (Th2).

ES 2246142 describes the effect of Domperidone in the treatment of Leishmaniosis, administered at a dose of 2 mg/kg/day on dogs infected with *L. Infantum*, by means of the reestablishment of the equilibrium between the cellular type immune response (Th1) and the humoral type immune response (Th2) through an increase of prolactine blood levels. It shows that, at this dose, Domperidone is able to reduce the clinical signs of Leishmaniosis and/or to reduce the level of antibodies in infected animals.

As far as we know, there have been no attempts in the state of the art in treating or preventing Leishmaniosis in healthy or infected mammals using domperidone at a dose regime below 2 mg/kg/day. We are not aware either of any treatment or prevention method using Domperidone at a dose regime below 2 mg/kg/day during the latent phase of the illness or during secondary events or outbreaks of the illness.

In Merck 1997, it is described a recommended dose of Domperidone of 1 mg/kg/day, however, this dose regimen is restricted to a different indication, namely as an antiemetic in dogs and not for the treatment of Leshmaniosis.

The review paper about canine Leishmaniosis and its therapeutic approaches, recently published by a group of world experts in this disease (Solano-Gallego et al. 2009. Vet Parasitol, 165:1-18), states that the decrease in the antibody titre is not commonly observed until 6 months (180 days) after the onset of the treatment when serology (titration of antibodies against *Leishmania*) is used to monitor conventional treatments (among them Alopurinol) of the disease.

"Recent studies have demonstrated a slow and progressive decrease in IgG and IgA antibody levels which is associated with clinical improvement. Therefore we recommend repeating a quantitative serological test in the same laboratory 6 months after the initial treatment due to the relatively long half live of IgG" (page 12)

"Some dogs would present a significant decrease in antibody levels associated with clinical improvement within 6 months to 1 year of treatment while others might not have a decrease in antibody titers despite the clinical improvement" (page 12)

It would be of great interest to develop an improved use of Domperidone for the treatment of Leishmaniosis or a method of treatment of Leishmaniosis allowing to decrease the unnecessary toxicity of the active ingredient, maintaining the same efficacy of the medicament observed at the higher dose regimens described in the art and/or allowing a faster decrease of the antibody titre in the treated mammals.

SUMMARY OF THE INVENTION

The present invention is based on the finding that domperidone or a pharmaceutically acceptable salt thereof may be used in a dosage regime or dose regimen, involving total daily amounts well below those so far suggested in the art to prevent and/or treat a disease associated with a decrease of the immune response. The use of lower dosage levels may allow minimization the occurrence of adverse effects.

Moreover, it has also been surprisingly found that the dosage regimes of the present invention allow obtaining a faster decrease of the antibody's titre in the treated subjects compared with that achieved using the treatments of the art.

Therefore, the present invention is directed to a method of treatment or prevention of Leshmaniosis in healthy or infected mammals using Domperidone with a dosage regime of 0.2-1 mg/kg/day having the same or greater efficacy than that achieved using the known dose regimes in the existing methods of treatment or prevention from the state of the art.

The present invention is also directed to prepare Domperidone formulations for the treatment or prevention of *Leshmaniosis* in healthy or infected mammals adapted to be used in a dose regime of 0.2-1 mg/kg/day providing the same or greater efficacy than that achieved using the known dose regimes in the existing methods of treatment or prevention from the state of the art.

The present invention is also directed to the use of Domperidone in combination with other drugs known to be useful for the treatment or prevention of *Leshmaniosis* in healthy or infected mammals (such as Leishmanicidal agents like N-methylglucamine antimoniate or Miltefosine, or such as Leishmaniostatic agents like Alopurinol) wherein the new Domperidone dosage regime provides the same or greater efficacy than that achieved using the known Domperidone dose regimes in the existing methods of treatment or prevention from the state of the art.

DETAILED DESCRIPTION OF THE INVENTION

It is one aspect of the present invention the use of domperidone or a pharmaceutically acceptable salt thereof for the preparation of a medicament for the treatment or prevention in a mammal of a disease associated with an alteration of the immune response wherein the medicament is prepared for the administration of a daily dose of domperidone is from 0.2 mg/kg/day to 1 mg/kg/day. It is further preferred that the medicament is prepared for the administration of a daily dose of domperidone of from 0.3 mg/kg/day to 0.7 mg/kg/day, more preferably from 0.45 mg/kg/day to 0.55 mg/kg/day and most preferably 0.5 mg/kg/day.

In one embodiment of the present invention the medicament is an oral dosage form intended for once a day administration. This embodiment facilitates adhesion of the patient to the therapeutic regime and thus compliance with this regime.

In an alternative embodiment of the present invention the medicament is an oral dosage form intended for twice a day administration.

In a preferred embodiment of the present invention the medicament is intended for use in the treatment of dogs.

In still another embodiment of the present invention domperidone is used in the form of its free base for the formulation of the medicament.

In an embodiment of the present invention the medicament is for the treatment or prevention in mammal of a disease associated to an alteration in cellular immunity mediated by CD4+Th1 lymphocytes. Examples of such diseases are:
  Leishmaniosis
  Parasitic diseases such as: malaria, other Trypanosomiasis, Ehrlichiosis, Toxoplasmosis and Coccidiosis,
  Immune diseases which progress with an increase in Th2 lymphocites and a decrease of Th1 such as asthma, atopies, hypersensitivity allergic reactions, and
  Viral diseases which progress with immunosuppression such as AIDS, herpesvirosis, adenovirosis, citomegalovirosis.

In a preferred embodiment of the present invention the medicament is for the treatment of leishmaniosis in mammal or to prevent its symptoms after infection has occurred.

In one embodiment of the present invention the medicament is prepared for the administration over a period of at least 10 days, preferably at least 15 days, more preferably at least 30 days.

The beneficial use of Domperidone or a pharmaceutically acceptable salt thereof in the treatment or prevention of Leshmaniosis in mammals (such as dogs) could be of high value when combined with a conventional treatment with a Leishmanicidal agent such as N-methylglucamine antimoniate or Miltefosine and/or a Leishmaniostatic agent such as Alopurinol.

In an embodiment of the invention Domperidone or a pharmaceutically acceptable salt thereof is used for the preparation of a medicament for the treatment or prevention in a mammal of a disease associated with an alteration of the immune response wherein the medicament is prepared for the combined administration of Alopurinol and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

The combined use may be facilitated by including all active ingredients in a single dosage form although it is also possible to use them in separate dosage forms.

In an embodiment of the present invention Domperidone or a pharmaceutically acceptable salt thereof is used for the preparation of a medicament for the treatment or prevention in a mammal of a disease associated with an alteration of the immune response wherein the medicament is prepared for the combined administration of N-methylglucamine antimoniate and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In an embodiment of the invention Domperidone or a pharmaceutically acceptable salt thereof is used for the preparation of a medicament for the treatment or prevention in a mammal of a disease associated with an alteration of the immune response wherein the medicament is prepared for the combined administration of Miltefosine and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

It is an embodiment of the invention the use of domperidone or a pharmaceutically acceptable salt thereof for the preparation of a medicament for the treatment or prevention in a mammal of a disease associated with an alteration of the immune response wherein the medicament is prepared for the combined administration of Alopurinol and N-methylglucamine antimoniate, and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

It is an embodiment of the invention the use of domperidone or a pharmaceutically acceptable salt thereof for the preparation of a medicament for the treatment or prevention in a mammal of a disease associated with an alteration of the immune response wherein the medicament is prepared for the combined administration of Alopurinol and Miltefosine, and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

Domperidone or a pharmaceutically acceptable salt thereof and the Leishmaniostatic agent or the leshmanicidal agent can either be administered in a single dosage form or in separate dosage forms.

It is another aspect of the present invention a method for treating or preventing in a mammal a disease associated with an alteration of the immune response which comprises the step of administering to such mammal domperidone or a pharmaceutically acceptable salt thereof at a daily dose of domperidone of from 0.2 mg/kg/day to 1 mg/kg/day. It is particularly preferred to administer a daily dose of domperidone from 0.3 mg/kg/day to 0.7 mg/kg/day, more preferably from 0.45 mg/kg/day to 0.55 mg/kg/day and most preferably 0.5 mg/kg/day.

In one embodiment of the present invention the method is characterized in that domperidone or a pharmaceutically acceptable salt thereof is administered as an oral dosage form intended for once a day administration which facilitates adhesion of the patient to the therapeutic regime and thus compliance with this regime.

In an alternative embodiment of the present invention the method is characterized in that domperidone or a pharmaceutically acceptable salt thereof is administered as an oral dosage form intended for twice a day administration.

In a preferred embodiment of the present invention the method is used to treat dogs.

In still another embodiment of the present invention the method is characterized in that domperidone or a pharmaceutically acceptable salt thereof is used in the form of its free base for its incorporation in a medicament prior to administration to the mammal.

In an embodiment of the present invention the method of treatment is used to treat or prevent a disease associated to an alteration in cellular immunity mediated by CD4+Th1 lymphocytes. In a preferred embodiment the disease is selected from the group comprising:

Leishmaniosis

Parasitic diseases such as: malaria, other Trypanosomiasis, Ehrlichiosis, Toxoplasmosis and Coccidiosis, Immune diseases which progress with an increase in Th2 lymphocites and a decrease of Th1 such as asthma, atopies, hypersensitivity allergic reactions, and Viral diseases which progress with immunosuppression such as AIDS, herpesvirosis, adenovirosis, citomegalovirosis.

In a preferred embodiment of the present invention the method of treatment is used to treat leishmaniosis or to prevent its symptoms after infection has occurred.

In one embodiment of the present invention the treatment is maintained over a period of at least 10 days, preferably at least 15 days, more preferably at least 30 days.

In an embodiment of the invention, the beneficial use of Domperidone or a pharmaceutically acceptable salt thereof in the treatment or prevention of Leshmaniosis in mammals (such as dogs) could be of high value when carried out after a conventional treatment with a Leishmanicidal agent like N-methylglucamine antimoniate or Miltefosine and/or a Leishmaniostatic agent like Alopurinol once the parasite charge has been reduced in the infected animal, helping thereby the animal in recovering an effective immunologic response to the illness.

In a preferred embodiment domperidone or a pharmaceutically acceptable salt thereof is administered in combination with a Leishmanicidal agent such as N-methylglucamine antimoniate or Miltefosine, both agents being administered either in a single dosage form or in separate dosage forms.

In another preferred embodiment domperidone or a pharmaceutically acceptable salt thereof is administered in combination with a Leishmaniostatic agent such as Alopurinol, both agents being administered either in a single dosage form or in separate dosage forms.

It is an embodiment of the invention a method for treating a mammal so as to increase the levels of prolactin in said mammal thereby preventing and/or treating a disease associated with an alteration of the immune response wherein said mammal is administered a combination comprising Alopurinol and a daily dose of domperidone or a pharmaceutically acceptable salt thereof from 0.2 mg/kg/day to 1 mg/kg/day. It is further preferred to administer a daily dose of domperidone is from 0.3 mg/kg/day to 0.7 mg/kg/day, more preferably from 0.45 mg/kg/day to 0.55 mg/kg/day and most preferably 0.5 mg/kg/day.

It is an embodiment of the invention a method for treating a mammal so as to increase the levels of prolactin in said mammal thereby preventing and/or treating a disease associated with an alteration of the immune response wherein said mammal is administered a combination comprising N-methylglucamine antimoniate and a daily dose of domperidone or a pharmaceutically acceptable salt thereof from 0.2 mg/kg/day to 1 mg/kg/day. It is further preferred to administer a daily dose of domperidone is from 0.3 mg/kg/day to 0.7 mg/kg/day, more preferably from 0.45 mg/kg/day to 0.55 mg/kg/day and most preferably 0.5 mg/kg/day.

It is an embodiment of the invention a method for treating a mammal so as to increase the levels of prolactin in said mammal thereby preventing and/or treating a disease associated with an alteration of the immune response wherein said mammal is administered a combination comprising Miltefosine and a daily dose of domperidone or a pharmaceutically acceptable salt thereof from 0.2 mg/kg/day to 1 mg/kg/day. It is further preferred to administer a daily dose of domperidone is from 0.3 mg/kg/day to 0.7 mg/kg/day, more preferably from 0.45 mg/kg/day to 0.55 mg/kg/day and most preferably 0.5 mg/kg/day.

It is an embodiment of the invention a method for treating a mammal so as to increase the levels of prolactin in said mammal thereby preventing and/or treating a disease associated with an alteration of the immune response wherein said mammal is administered a combination comprising Alopurinol and N-methylglucamine antimoniate and a daily dose of domperidone or a pharmaceutically acceptable salt thereof from 0.2 mg/kg/day to 1 mg/kg/day. It is further preferred to administer a daily dose of domperidone is from 0.3 mg/kg/day to 0.7 mg/kg/day, more preferably from 0.45 mg/kg/day to 0.55 mg/kg/day and most preferably 0.5 mg/kg/day.

It is an embodiment of the invention a method for treating a mammal so as to increase the levels of prolactin in said mammal thereby preventing and/or treating a disease associated with an alteration of the immune response wherein said mammal is administered a combination comprising Alopurinol and Miltefosine and a daily dose of domperidone or a pharmaceutically acceptable salt thereof from 0.2 mg/kg/day to 1 mg/kg/day. It is further preferred to administer a daily dose of domperidone is from 0.3 mg/kg/day to 0.7 mg/kg/day, more preferably from 0.45 mg/kg/day to 0.55 mg/kg/day and most preferably 0.5 mg/kg/day.

Domperidone or a pharmaceutically acceptable salt thereof and the Leishmaniostatic agent or the leshmanicidal agent can either be administered in a single dosage form or in separate dosage forms.

It is one aspect of the present invention a composition comprising domperidone or a pharmaceutically acceptable salt thereof for use in the treatment or prevention in a mammal of a disease associated with an alteration of the immune response wherein the composition is prepared for the administration of a daily dose of domperidone of from 0.2 mg/kg/day to 1 mg/kg/day. It is further preferred that the composition is prepared for the administration of a daily dose of domperidone of from 0.3 mg/kg/day to 0.7 mg/kg/day, more preferably from 0.45 mg/kg/day to 0.55 mg/kg/day and most preferably 0.50 mg/kg/day.

In one embodiment of the present invention the composition is prepared as an oral dosage form for once a day administration. This embodiment facilitates adhesion of the patient to the therapeutic regime and thus compliance with this regime.

In an alternative embodiment of the present invention is characterized in that the composition is administered as an oral dosage form intended for twice a day administration.

In an embodiment the composition is for the treatment or prevention of a disease associated with an alteration of the immune response in a dog.

In still another embodiment the composition comprises domperidone in the form of the free base.

In another embodiment of the present invention the composition is for use in the treatment or prevention of a disease associated with an alteration of the immune response, preferably the disease is selected from the group of diseases associated to an alteration in cellular immunity mediated by CD4+Th1 lymphocytes. It is further preferred that the disease is selected from the group comprising:

Leishmaniosis

Parasitic diseases such as: malaria, other Trypanosomiasis, Ehrlichiosis, Toxoplasmosis and Coccidiosis, Immune diseases which progress with an increase in Th2 lymphocites and a decrease of Th1 such as asthma, atopies, hypersensitivity allergic reactions, and Viral diseases which progress with immunosuppression such as AIDS, herpesvirosis, adenovirosis, citomegalovirosis.

In a more preferred embodiment the composition is for use in the treatment of leishmaniosis or in the prevention of its symptoms after infection has occurred.

In still another embodiment the composition is prepared for the administration over a period of at least 10 days, preferably 15 days, more preferably 30 days.

The composition is beneficially used in the treatment or prevention of Leshmaniosis in mammals (such as dogs) and could be of high value when combined with a conventional treatment with a Leishmanicidal agent such as N-methylglucamine antimoniate or Miltefosine and/or a Leishmaniostatic agent such as Alopurinol.

In an embodiment of the invention the composition is prepared for use in the treatment or prevention in a mammal of a disease associated with an alteration of the immune response wherein the composition is prepared for the combined administration of Alopurinol and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In an embodiment of the invention the composition is prepared for use in the treatment or prevention in a mammal of a disease associated with an alteration of the immune response wherein the composition is prepared for the combined administration of N-methylglucamine antimoniate and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In an embodiment of the invention the composition is prepared for use in the treatment or prevention in a mammal of a disease associated with an alteration of the immune response wherein the composition is prepared for the combined administration of Miltefosine and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In an embodiment of the invention the composition is prepared for used for the treatment or prevention in a mammal of a disease associated with an alteration of the immune response and it is prepared for the combined administration of Alopurinol and N-methylglucamine antimoniate, and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In an embodiment of the invention the composition is prepared for use in the treatment or prevention in a mammal of a disease associated with an alteration of the immune response and it is prepared for the combined administration of Alopurinol and Miltefosine, and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In still another embodiment of the invention the composition is prepared for the combined administration of domperidone or a pharmaceutically acceptable salt thereof and a leishmanicidal agent such as N-methylglucamine antimoniate or Miltefosine, preferably the composition comprises both agents either in a single dosage form or in separate dosage forms.

In still another embodiment of the invention the composition is prepared for the combined administration of domperidone or a pharmaceutically acceptable salt thereof and a Leishmaniostatic agent such as Alopurinol, preferably the composition comprises both agents either in a single dosage form or in separate dosage forms.

The composition of Domperidone or a pharmaceutically acceptable salt thereof and the Leishmaniostatic agent or the leshmanicidal agent can either be administered in a single dosage form or in separate dosage forms.

In one aspect of the present invention domperidone or a pharmaceutically acceptable salt thereof is for use in the treatment or prevention in a mammal of a disease associated with an alteration of the immune response at a daily dose of domperidone of from 0.2 mg/kg/day to 1 mg/kg/day. It is further preferred to use it at a daily dose of domperidone of from 0.3 mg/kg/day to 0.7 mg/kg/day, more preferably from 0.45 mg/kg/day to 0.55 mg/kg/day and most preferably 0.50 mg/kg/day.

In one embodiment of the present invention domperidone or a pharmaceutically acceptable salt thereof is for use in the form of an oral dosage form for once a day administration. This embodiment facilitates adhesion of the patient to the therapeutic regime and thus compliance with this regime.

In an alternative embodiment of the present invention domperidone or a pharmaceutically acceptable salt thereof is for use as an oral dosage form intended for twice a day administration.

In an embodiment domperidone or a pharmaceutically acceptable salt thereof is for use in the treatment or prevention of a disease associated with an alteration of the immune response in a dog.

In still another embodiment the domperidone or a pharmaceutically acceptable salt thereof is for use in the form of the free base.

In another embodiment of the present invention domperidone or a pharmaceutically acceptable salt thereof is for use in the treatment or prevention of a disease associated with an alteration of the immune response, preferably the disease is selected from the group of diseases associated to an alteration in cellular immunity mediated by CD4+Th1 lymphocytes. It is further preferred that the disease is selected from the group comprising:

Leishmaniosis

Parasitic diseases such as: malaria, other Trypanosomiasis, Ehrlichiosis, Toxoplasmosis and Coccidiosis, Immune diseases which progress with an increase in Th2 lymphocites and a decrease of Th1 such as asthma, atopies, hypersensitivity allergic reactions, and Viral diseases which progress with immunosuppression such as AIDS, herpesvirosis, adenovirosis, citomegalovirosis.

In a more preferred embodiment domperidone or a pharmaceutically acceptable salt thereof is for use in the treatment of leishmaniosis or in the prevention of its symptoms after infection has occurred.

In still another embodiment domperidone or a pharmaceutically acceptable salt thereof is for use in the administration over a period of at least 10 days, preferably 15 days, more preferably 30 days.

Domperidone or a pharmaceutically acceptable salt thereof is beneficially used in the treatment or prevention of Leshmaniosis in mammals (such as dogs) and could be of high value when combined with a conventional treatment with a Leishmanicidal agent such as N-methylglucamine antimoniate or Miltefosine and/or a Leishmaniostatic agent such as Alopurinol.

In an embodiment of the invention domperidone or a pharmaceutically acceptable salt thereof is for use in the treatment or prevention in a mammal of a disease associated with an alteration of the immune response wherein it is prepared for the combined administration of Alopurinol and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In an embodiment of the invention domperidone or a pharmaceutically acceptable salt thereof is for use in the treatment or prevention in a mammal of a disease associated with an alteration of the immune response wherein it is prepared for the combined administration of N-methylglucamine antimoniate and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In an embodiment of the invention domperidone or a pharmaceutically acceptable salt thereof is for use in the treatment or prevention in a mammal of a disease associated with an alteration of the immune response wherein it is prepared for the combined administration of Miltefosine and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In an embodiment of the invention domperidone or a pharmaceutically acceptable salt thereof is for use in the treatment or prevention in a mammal of a disease associated with an alteration of the immune response and it is prepared for the combined administration of Alopurinol and N-methylglucamine antimoniate, and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In an embodiment of the invention domperidone or a pharmaceutically acceptable salt thereof is for use in the treatment or prevention in a mammal of a disease associated with an alteration of the immune response and it is prepared for the combined administration of Alopurinol and Miltefosine, and a daily dose of domperidone of from 0.2 mg/kg/day to 1 mg/kg/day, preferably from 0.3 mg/kg/day to 0.7 mg/kg/day, more preferably from 0.45 mg/kg/day to 0.55 mg/kg/day, most preferred 0.5 mg/kg/day.

In still another embodiment of the invention domperidone or a pharmaceutically acceptable salt thereof is for use in combined administration with a leishmanicidal agent such as N-methylglucamine antimoniate or Miltefosine, preferably by combined administration with both agents either in a single dosage form or in separate dosage forms.

In still another embodiment of the invention domperidone or a pharmaceutically acceptable salt thereof is for used in combined administration with a Leishmaniostatic agent such as Alopurinol, preferably by combined administration with both agents either in a single dosage form or in separate dosage forms.

Domperidone or a pharmaceutically acceptable salt thereof and the Leishmaniostatic agent or the leshmanicidal agent can either be administered in a single dosage form or in separate dosage forms.

The active compounds may be administered orally in the any suitable dosage form such as syrups, tablets, capsules, lozenges, controlled-release preparations, fast-dissolving preparations, lozenges, etc) or by injection (subcutaneous, intradermic, intramuscular, intravenous, etc.).

Formulations for injection administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent.

Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

The pharmaceutical formulations may conveniently be presented in unit dosage form and may be prepared by any of the methods well known in the art of pharmacy. All methods include the step of bringing the active ingredient (s) association with the carrier. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example natural, synthetic or semisynthetic oils or water with flavouring, sweetener and/or colouring agent.

Where the composition is in the form of a tablet, any pharmaceutical carrier routinely used for preparing solid formulations may be used.

A tablet may be made by compression or moulding, optionally with one or more accessory ingredients. Compressed tablets may be prepared by compressing in a suitable machine the active ingredient in a free-flowing form such as a powder or granules, optionally mixed with binders, lubricants, inert diluents, lubricating, surface active or dispersing agents. Moulded tablets may be made by moulding in a suitable machine a mixture of the powdered blend comprising the active compounds moistened with an inert liquid diluent and optionally dried and sieved. The tablets may optionally be coated or scored and may be formulated so as to provide modified (i.e. slow or controlled) release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered.

DEFINITIONS AND CONVENTIONS

The definitions and explanations below are for the terms as used throughout this entire document including both the specification and the claims.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

The term pharmaceutically acceptable salt embraces salts with a pharmaceutically acceptable acid or base. Pharmaceutically acceptable acids include both inorganic acids, for example hydrochloric, sulfuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic, cyclohexylsulfamic (cyclamic) or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

In the context of infectious diseases the term prevention is not used to designate avoidance of infection of the patient with the infectious agent but the avoidance of the appearance of the clinical signs associated with disease progression after infection has occurred.

When quantities or doses of Domperidone or pharmaceutically stable salts thereof are mentioned in this application they refer to the quantities or doses expressed as Domperidone free base.

The term treatment is used to designate the control of disease progression once the clinical signs had appeared.

The present invention exhibits the advantages of reducing unnecessary toxicological effects of the drug when administered at higher doses to the mammal.

In case the dosage regime is administered once daily, this has the additional advantage of facilitating the compliance of the therapeutic dosage regimen (it is easier and more convenient to administer the medicament once daily).

A leshmanicidal agent is referred to an agent, which is able to kill the parasite which causes Leshmaniosis. A leshmaniostatic agent is referred to an agent, which does not kill the parasite which causes Leshmaniosis but instead is able to prevent its reproduction.

By "combined administration", it has to be understood that Domperidone can be administered together or separately, simultaneously, concurrently or sequentially with a Leishmanicidal agent like N-methylglucamine antimoniate or Miltefosine and/or a Leishmaniostatic agent like Alopurinol in any order, e.g. the administration of Domperidone can be made first, followed by the administration of the Leishmanicidal agent and/or the Leishmaniostatic agent, or the administration of Domperidone can be made last, preceded by the administration of the Leishmaniostatic agent and/or the Leishmanicidal agent; or the administration of Domperidone can be made concomitantly with the Leishmaniostatic agent and/or the Leishmanicidal agent.

By "synergistic effect between Domperidone and Alopurinol", it has to be understood the effect observed on the clinical improvement of the disease when both drugs are administered together. Specifically, it is observed that the decrease in the antibody titre against *Leishmania* decreases faster when both drugs are administered in combination than when each drug is administered separately.

EXAMPLES

The advantages of the invention are more fully illustrated with reference to the following examples.

Example 1

Kinetic Profile Study of the Prolactine Hormone after Domperidone Oral Administration in Beagle Male Dog The present study was performed with the objective of determining the kinetic profile of the prolactine hormone in male dog after oral administration of domperidone at different dosage levels. 10 animals where used, which received a single oral administration of domperidone at six different dosage levels (0.125 mg/kg, 0.250 mg/kg, 0.5 mg/kg, 1 mg/kg, 2 mg/kg and 4 mg/kg) as well as a placebo, following a crossover trial in 7 phases separated by a minimal washing out period of 6 days. During each of the 7 phases blood samples were extracted at different times (t=0 h, 0.5 h, 1 h, 2 h, 4 h, 6 h, 8 h, 10 h, 12 h, 18 h, 36 y 48 h) for determining serum concentrations of prolactine using a commercial immuno enzymatic assay kit.

Although all the dosages produced a fast increase in the average concentrations of prolactine in blood, this increase was lower in the two lower dosage levels (0.125 and 0.250 mg/kg). With higher dosage levels (0.5 mg/kg, 1 mg/kg, 2 mg/kg and 4 mg/kg) increase was more pronounced but similar between them, not being possible to observe dose-effect correlation. In all cases the average concentrations of prolactine in the first 36 hours after domperidone administration remained above the prolactine concentration in the group treated with the placebo.

The greater values for the area under the curve of prolactine calculated between 0 h and 12 h (AUC) were obtained after the administration of domperidone at levels of 0.5 mg/kg and above. However, the values obtained after the administration at 1 mg/kg, 2 mg/kg and 4 mg/kg were not significantly greater than those obtained with the 0.5 mg/kg dosage.

In addition, the greater values of maximum concentration of prolactine (Cmax) were also obtained after the administration of domperidone at levels of 0.5 mg/kg dosage and above. Once again, the values obtained after its administration at 1 mg/kg, 2 mg/kg and 4 mg/kg were not significantly greater than those obtained with the 0.5 mg/kg dosage.

Finally, the time required to reach maximum prolactine concentration (Tmax) when domperidone was administered at levels of 0.5 mg/kg and above was lower than the time required after its administration at lower dosages (0.125 mg/kg and 0.250 mg/kg). In this case no statistically significant differences were observed between the 6 dosages studied.

Table 1 summarizes the mean values for AUC-12 h obtained in the six groups of treatment. The groups in front of which significant differences were observed are indicated ($p<0.05$) in the last column of each group.

TABLE 1

|  | Group | Dosage | Mean | Est. Signific. Dif. vs. groups |
|---|---|---|---|---|
| AUC 0-12 | A | Placebo | 9.4 | B, C, D, E, F, G |
| (ng · h/ml) | B | 0.5 mg/kg | 101.3 | A, F, G |
|  | C | 1 mg/kg | 110.2 | A, F, G |
|  | D | 2 mg/kg | 97.6 | A, F, G |
|  | E | 4 mg/kg | 107.4 | A, F, G |
|  | F | 0.125 mg/kg | 69.0 | A, B, C, D, E |
|  | G | 0.250 mg/kg | 63.0 | A, B, C, D, E |

Table 2 summarizes the mean values for $C_{max}$ obtained in the six groups of treatment. The groups in front of which significant differences were observed are indicated ($p<0.05$) in the last column of each group.

TABLE 2

|  | Group | Dosage | Mean | Est. Signific. Dif. vs. groups |
|---|---|---|---|---|
| $C_{max}$ | A | Placebo | 2.1 | B, C, D, E, F, G |
| (ng/ml) | B | 0.5 mg/kg | 12.9 | A, F, G |
|  | C | 1 mg/kg | 15.1 | A, F, G |
|  | D | 2 mg/kg | 13.6 | A, F, G |
|  | E | 4 mg/kg | 14.2 | A, F, G |
|  | F | 0.125 mg/kg | 7.8 | A, B, C, D, E |
|  | G | 0.250 mg/kg | 7.7 | A, B, C, D, E |

Table 3 summarizes the mean values for $T_{max}$ obtained in the six groups of treatment. The groups in front of which significant differences were observed are indicated ($p<0.05$) in the last column of each group.

TABLE 3

|  | Group | Dosage | Mean | Est. Signific. Dif. vs. groups |
|---|---|---|---|---|
| $T_{max}$ | A | Placebo | 19.0 | B, C, D, E, F, G |
| (h) | B | 0.5 mg/kg | 3.7 | A |
|  | C | 1 mg/kg | 2.7 | A |
|  | D | 2 mg/kg | 5.0 | A |
|  | E | 4 mg/kg | 4.6 | A |
|  | F | 0.125 mg/kg | 8.6 | A |
|  | G | 0.250 mg/kg | 7.2 | A |

The results surprisingly show that it is possible to administer dosage levels of domperidone to dogs below those described in the art (1 mg/kg/administration) while inducing the production of prolactine at levels comparable with those produced at the higher dosage described in the art. This effect is confirmed at dosages as small as 0.5 mg/kg.

Example 2

Study of the Effect of Domperidone Administration on the Cellular Immune Response in Healthy Dogs The present study was undertaken to prove the effect of domperidone administration on the cellular immune response in healthy dogs through a controlled trial. 20 dogs of different breed, sex and age, were randomly distributed into two groups of 10. Animals from one of two groups worked as a negative control and did not receive any treatment. Animals from the other group received 0.5 mg domperidone/kg/day, orally, during 30 consecutive days. During the study several visits were paid (days 0, 15, 30, 60 and 90) during which some clinical examinations were done and blood samples were collected for biochemical, haematological and serological analyses (DAT). The percentages of activated monocytes and neutrophils were determined in whole blood samples through the nitroblue tetrazolium (NBT) reduction test.

Table 4 summarizes the mean values of the percentage of activated monocytes in the two groups compared by Student's t test.

TABLE 4

| Monocytes | | | |
|---|---|---|---|
|  | Group A n = 10 % | Group B (Treated) n = 10 % | Statistical comparison |
| Day 0 | 3.400 | 3.200 | 0.6764 |
| Day 15 | 3.400 | 26.10 | p < 0.0001 |
| Day 30 | 3.300 | 26.40 | p < 0.0001 |
| Day 60 | 3.800 | 8.600 | p < 0.0001 |
| Day 90 | 3.200 | 3.100 | 0.8558 |

Table 5 summarizes the mean values of the percentage of activated neutrophils in the two groups, compared by t Student's t test.

TABLE 5

| Neutrophils | | | |
|---|---|---|---|
|  | Group A n = 10 % | Group B (Treated) n = 10 % | Statistical comparison |
| Day 0 | 5.900 | 5.700 | 0.8354 |
| Day 15 | 5.700 | 38.50 | p < 0.0001 |
| Day 30 | 5.200 | 40.00 | p < 0.0001 |
| Day 60 | 4.600 | 15.10 | p < 0.0001 |
| Day 90 | 6.000 | 5.900 | 0.9115 |

The results showed that in the group that did not receive any treatment the percentage of activated monocytes and neutrophils remained low and stable during the 90 monitored days. However, animals treated with domperidone suffered a statistically significant increase during the treatment, remaining high during at least 30 days after finishing the treatment.

The results surprisingly showed that domperidone administration at a dosage of 0.5 mg/kg/day on healthy dogs during 30 consecutive days, produced a stimulating effect of the cellular immune response that persists at least a month after finishing the treatment.

Example 3

Study of the Response of the Circulating Monocyte-Derived Macrophages from Healthy Dog Treated with Domperidone, to the In Vitro Infection with *Leishmania infantum*

The objective of this study is to assess the effect of domperidone on the susceptibility to infection and the in vitro leishmanicidal capacity of circulating monocyte-derived macrophages exposed to *Leishmania infantum* promastigotes.

It is designed as a prospective monocentric study. A total of 10 dogs have been included, each of them acting as its own control, for which reason it has not been considered necessary the use of a negative control. All the animals received domperidone orally at a dosage of 0.5 mg/kg/day during 30 consecutive days. During the study several visits are paid the days 0 (basal), 15 and 30 of treatment, and days 60 and 90 (one and two months after finishing the treatment, respectively). During each visit blood is collected from animals and it is processed to isolate and culture monocytes-macrophages, which are then co-cultivated with *Leishmania* promastigotes. After 48 hours the nitroblue tetrazolium (NBT) reduction test is carried out on the cultures and the percentage of parasited macrophages and the number of amastigotes per macrophage were measured. Blood samples are also collected on days 0 and 90 to assess animal health by biochemical and haematological analyses.

Table 6 summarizes the percentage of macrophages infected after 48 hours of in vitro culture with *Leishmania infantum* promastigotes.

TABLE 6

|  | MEAN | Statistical comparison vs Day 0 |
|---|---|---|
| Day 0 | 89.0 | — |
| Day 15 | 27.2 | $p < 0.05$ |
| Day 30 | 24.4 | $p < 0.05$ |
| Day 60 | 82.6 | NS |
| Day 90 | 89.5 | NS |

NS = Non-significant differences

Table 7 summarizes the percentage of positive NBT macrophages after 48 hours of co-culture with *Leishmania infantum* promastigotes.

TABLE 7

|  | MEAN | Statistical comparison vs day 0 |
|---|---|---|
| Day 0 | 2.00 | — |
| Day 15 | 61.10 | $p < 0.05$ |
| Day 30 | 62.20 | $p < 0.05$ |
| Day 60 | 1.70 | NS |
| Day 90 | 1.80 | NS |

NS = Non-significant differences

Table 8 summarizes the number of amastigotes per macrophage after 48 hours of in vitro co-culture with *Leishmania infantum* promastigotes differences

TABLE 8

|  | MEAN | Statistical comparison vs Day 0 |
|---|---|---|
| Day 0 | 44.4 | — |
| Day 15 | 9.7 | $p < 0.05$ |
| Day 30 | 11.3 | $p < 0.05$ |
| Day 60 | 23.1 | $p < 0.05$ |
| Day 90 | 42.6 | NS |

NS = Non-significant

These results have showed a significant increase of the phagocytic activity (NBT positive macrophages, Table 7) in the macrophages in the samples collected on days 15 and 30, even though the percentages of activated macrophages returned to their normal basic values in the samples collected on days 60 and 90. In parallel, and in concordance with the present results, the average percentage of infected macrophages, which in the cell culture from samples collected on day 0 was around 90%, decreased significantly down to around 25% in samples collected on days 15 and 30, returning thereby to values close to the basic ones in samples collected on days 60 and 90 (Table 6). Finally, the number of amastigotes per infected macrophage followed a dynamic similar to the one described for the other two parameters (Table 8).

According to the obtained results, it can be concluded that the daily administration of 0.5 mg/kg of Domperidone in dogs prepares the main cells involved in unspecific immunity (monocytes/macrophages) to an effective activation against infection by *Leishmania*, in experimental in-vitro conditions.

Example 4

Study of the Clinical Efficacy of a Treatment Plan with Domperidone Against Canine Leishmaniosis in its Incipient Stages The objective of this study is the evaluation of the efficacy of an oral treatment plan with domperidone against canine leishmaniosis in its incipient stages, assessing its effect on the clinical illness incidence in a population of healthy animals resident in a highly endemic area.

It is designed as a field controlled clinical trial (treated group vs non-treated group) with 100 initially healthy animals (non-infected) resident in a highly endemic area, therefore with high possibilities to be infected. Half of the animals have received domperidone at a dosage of 0.5 mg/kg/day in accordance with a treatment plan that consists of repeatedly administering domperidone during periods of 30 days each four months ensuring that the treatment covers the onset and the end of the activity period of the transmitter insect to guarantee a double objective: In the first place reinforcing primary cellular response of the dog, so that when the insect infects the animal its primary defense barrier is prepared to beat the parasites resistance, to destroy them and to develop a specific immune response appropriate for the illness control/elimination. In the second place balancing the immune response of the animals which, having been infected during the periods of lower protection, are still in the initial phase of the illness.

Table 9 summarizes the accumulated percentage of animals with signs of canine Leishmaniosis at the end of the study (second year of monitoring)

TABLE 9

|  | Animals WITH signs of canine Leishmaniosis | Animals WITHOUT signs of canine Leishmaniosis | Statistical comparison |
|---|---|---|---|
| Non-treated group (n = 46) | 50% | 50% | $p < 0.001$ |
| Treated group (n = 45) | 11% | 85% |  |

As it is showed in the table, after 2 years 50% of the animals in the non-treated group presented indicative signs of the illness progress whereas in the treated group said percentage was statistically lower (only 11% of the animals that also presented positive serology only against *Leishmania* but no clinical signs, unlike the non-treated group).

From the results it is concluded that the treatment plan applied in the present study to healthy animals resident in a highly endemic area means a statistically significant decrease in the number of ill animals after 2 years, confirming its clinical efficacy in the prevention of canine Leishmaniosis.

Example 5

Study of the Clinical Efficacy and Security of a Treatment Plan with Domperidone for the Control of Canine Leishmaniosis in Low Incidence Areas In order to assess the efficacy of an oral treatment plan based on Domperidone for the control of canine Leishmaniosis, a controlled study was performed with 240 seronegative animals against *Leishmania* resident in an endemic geographical area.

The study lasted for 9 months, beginning at the onset of the activity period of the vector insect in the geographical area in which animals were found and closing three months after the end of this period. The presence of the vector was confirmed before starting the treatment.

Half of the animals (n=120) received two treatments during 30 days at 0.5 mg/kg/day of Domperidone orally, one at the onset and the other at the end of the activity period of the vector.

The remaining 120 animals received a placebo under an equivalent dosage regime.

Along the study most dogs presented a normal clinical state except several animals of both groups of treatment, which suffered from superficial wounds accompanied by a slight lymphadenopathy as a consequence of fights, and seven animals from the non-treated group in which the appearance of lymphadenopathy and allopecia during the last month of monitoring was observed. In the control performed at the end of the study, the same 7 animals in which lymphadenopathy and allopecia had been observed showed seropositivity against *Leishmania* (DAT≥1/400) whereas all animals from the treated group were negative. The observed differences were statistical significant (5.83% vs 0%). In the 7 seropositive cases the illness was confirmed by direct observation of *Leishmania* amastigotes inside macrophages in any of the lymph node or bone marrow samples obtained by fine needle aspirate (FNA). None of the animals of the treated group showed clinical symptoms indicative of adverse reactions attributable to the administration of the medication during the study.

Table 10 shows the accumulated percentage of animals with signs of canine Leishmaniosis at the end of the study (9th month of monitoring).

TABLE 10

|  | Animals WITH signs of canine Leishmaniosis | Animals WITHOUT signs of canine Leishmaniosis | Statistical comparison |
| --- | --- | --- | --- |
| Non-treated group (n = 120) | 5.8% | 94.2% | p < 0.001 |
| Treated group (n = 120) | 0 | 100% |  |

The results obtained confirm the efficacy and security of the dosage treatment used in the present study for the control of canine Leishmaniosis in animals resident in an endemic geographical area.

Example 6

Study of the Clinical Efficacy of Domperidone Alone in the Treatment of Canine Leishmaniosis A clinical study was performed including a group of 70 dogs with an initial stage of Leishmaniosis (antibody titre against *Leishmania* between 1/800 and 1/1600-threshold of positively 1/800-and oligosymptomatics). All animals were treated with Domperidone, orally during 30 consecutive days, at a dose of 1 mg/kg/12 h (the animals having a weight lower than 30 kg) or at a dose of 0.7 mg/kg/12 h (the remaining animals).

All animals were submitted to several clinical controls at 30, 90 and 180 days after the onset of the treatment, and they were also submitted to a basal control. During said controls different immunological (antibody titre against *Leishmania*-DAT, intradermoreaction test-Leishmanina), clinical (clinical symptoms, body weight) and analytical (biochemical profile, haematology, proteinogram and urine test for the determination of UPC ratio) parameters were assessed.

The assessment of the efficacy of the treatment was performed from the global evaluation of all parameters, but paying special attention to the evolution of antibody titre (Ac) against *Leishmania* and to the evolution of clinical symptoms and specifically to the lymphadenopathy, a symptom showed by all animals to a greater or lesser degree in the moment of their inclusion in the study.

Table 11 summarizes the percentage dogs that showed an antibody titre lower than the antibody titre at day 0.

TABLE 11

|  | DAY 30 | DAY 90 | DAY 180 |
| --- | --- | --- | --- |
| Antibody titre lower than DAY 0 | 10% | 47% | 57% |

The results prove that the treatment was effective to slow down the evolution of the disease. The antibody titre decreased in 47% of the animals after 90 days from the onset of the treatment while in any case an increase was produced. Said percentage had increased to 57% at 180 days.

These observations show that when Domperidone is administered alone the decrease of antibodies against *Leishmania* is faster than the decrease described in the bibliography for treatments with other drugs such as Alopurinol (180 days in the case of alopurinol).

Moreover, clinical symptoms (mainly the lymphadenopathy) decreased progressively until total disappearance in 100% animals in the course of the 12 months after the onset of the treatment.

In general the treatment entails a clear decrease and/or stabilization of both antibody titre and clinical symptoms associated to Leishmaniosis, said phenomenon being able to be attributed to an indirect immunomodulator effect of the molecule whose final result consists on a change of the immune response from Th2 to Th1.

The experimental data of animals treated with Domperidone show that although at day 180 the 57% of treated animals experimented a decrease in the antibody titre against *Leishmania*, at day 90 the 47% of animals experimented said decrease, indicating that the administration of Domperidone entails a clear advantage over the administration of conventional treatments, accelerating the decrease in the antibody titre against *Leishmania*.

Example 7

Study of the Synergistic Effect of Domperidone and Alopurinol in the Treatment of Canine Leishmaniosis Seven dogs with clinical symptoms compatibles with leishmaniosis (lymphadenomegaly, loss of weight, allopecia, . . . ), positive antibody titre in the direct agglutination test (DAT) (cut off≥1/400) and direct identification by fine needle puncture of popliteal lymph node or bone marrow were included in the study. Domperidone was administered to all of them at a dose 0.5 mg/kg/24 h during one consecutive month and Alopurinol at 10 mg/kg/12 h during three months. For the efficacy assessment a clinical monitoring was performed during three months, monitoring the main symptoms related to the disease (cutaneous lesions, lymphadenomegaly, progressive loss of weight, muscle atrophy, exercise intolerance, epistaxis, limp, onicogriphosis) and also a DAT serology at days 30 and 90.

The results obtained regarding the clinical monitoring and the level of antibodies were:

The seven dogs had a significant improvement regarding the basal visit both at day 30 and at day 90.

In the seven animals a significant decrease in the antibody titre at day 90 in front of the basal level was observed.

Four of seven dogs had negative serology at the end of the study.

Table 12 summarises the percentage of dogs showing an antibody titre lower than at day 0 at days 30, 90 and 180 determined using the Direct Agglutination Test (DAT).

TABLE 12

|  | DAY 30 | DAY 90 |
| --- | --- | --- |
| Antibody titre lower than DAY 0 | 42.8% | 100% |

At day 30, 42.8% of the dogs show an antibody titre lower than at day 0. At day 90 this percentage increased to 100%.

The prognosis of a dog suffering leishmaniosis is determined by its immunitary response. Any treatment capable of correcting the imbalance in this response affects the key point of the disease.

For this study two drugs have been used. These drugs achieve good results separately, by immunoestimulation (Domperidone) and reduction of the parasite activity (Alopurinol). By their association, this combination is very effective in the treatment of canine leishmaniosis producing a clinical improvement and a fast decrease in the level of antibodies. The resultant synergy provides a response more efficient and faster.

Experimental data of animals treated with Domperidone and Alopurinol show that at day 90 the 100% of treated animals experimented a decrease in the antibody titre against *Leishmania* (unlike the previous study wherein at day 90 only a 47% of animals experimented said decrease), showing a clear synergistic effect over the evolution of the disease when both drugs are combined.

It has been surprisingly observed that the combination of Alopurinol and Domperidone may reduce the antibody titre well in advance of the 180 days period mentioned in the art (Solano-Gallego) when Domperidone is used alone at conventional doses.

The invention claimed is:

1. A method of treatment of leishmaniosis in a mammal or decreasing the likelihood of the clinical symptoms of leishmaniosis in a mammal, comprising administering to a mammal in need thereof domperidone or a pharmaceutically acceptable salt thereof at a daily dose of domperidone of from 0.2 mg/kg/day to 1 mg/kg/day.

2. The method according to claim 1, wherein domperidone is administered at a daily dose of from 0.3 mg/kg/day to 0.7 mg/kg/day.

3. The method according to claim 2, wherein domperidone is administered at a daily dose of from 0.45 mg/kg/day to 0.55 mg/kg/day.

4. The method according to claim 3, wherein domperidone is administered at a daily dose of 0.50 mg/kg/day.

5. The method according to claim 1, wherein domperidone is administered orally once a day.

6. The method according to claim 1, wherein the mammal is a dog.

7. The method according to claim 1, wherein domperidone is administered in the form of free base.

8. The method according to claim 1, wherein domperidone is administered over a period of at least 10 days.

9. The method according to claim 8, wherein domperidone is administered over a period of at least 15 days.

10. The method according to claim 9, wherein domperidone is administered over a period of at least 30 days.

11. The method according to claim 1, wherein domperidone is administered in combination with a leishmanicidal agent.

12. The method according to claim 11, wherein domperidone and the leishmanicidal agent are administered either in a single dosage form or in separate dosage forms.

13. The method according to claim 1, wherein domperidone is administered in combination with a leishmaniostatic agent.

14. The method according to claim 13, wherein domperidone and the leishmaniostatic agent are administered either in a single dosage form or in separate dosage forms.

15. The method according to claim 11, wherein the leishmanicidal agent is at least one selected from the group consisting of N-methylglucamine antimoniate and Miltefosine.

16. The method according to claim 13, wherein the leishmaniostatic agent is Allopurinol.

* * * * *